(12) United States Patent
Batullin et al.

(10) Patent No.: US 9,192,893 B2
(45) Date of Patent: Nov. 24, 2015

(54) METHOD FOR PRODUCING HIGH PURITY CRYSTALLINE CARBAMIDE

(71) Applicants: Farid Alekovich Batullin, Naberezhnye Chelny (RU); Andrei Vladimirovich Andreev, Ufimsky (RU)

(72) Inventors: Farid Alekovich Batullin, Naberezhnye Chelny (RU); Andrei Vladimirovich Andreev, Ufimsky (RU)

(*) Notice: Subject to any disclaimer, the term of this patent is extended or adjusted under 35 U.S.C. 154(b) by 0 days.

(21) Appl. No.: 14/360,347

(22) PCT Filed: Dec. 3, 2012

(86) PCT No.: PCT/RU2012/001014
§ 371 (c)(1),
(2) Date: May 23, 2014

(87) PCT Pub. No.: WO2013/077775
PCT Pub. Date: May 30, 2013

(65) Prior Publication Data
US 2014/0332388 A1     Nov. 13, 2014

(30) Foreign Application Priority Data
Nov. 23, 2011   (RU) .................................. 2011147680

(51) Int. Cl.
*B01D 61/42*     (2006.01)
*B01D 61/58*     (2006.01)
*C07C 273/16*    (2006.01)

(52) U.S. Cl.
CPC .............. *B01D 61/422* (2013.01); *B01D 61/58* (2013.01); *C07C 273/16* (2013.01)

(58) Field of Classification Search
CPC ..... B01D 61/422; B01D 61/58; C07C 273/16
USPC ............. 204/450, 518, 527, 543, 544; 564/73
See application file for complete search history.

(56) References Cited

U.S. PATENT DOCUMENTS 2,892,870 A *  6/1959  Matile .............................. 564/73
3,287,407 A * 11/1966  Zardi ............................... 564/73

FOREIGN PATENT DOCUMENTS

RU         2041202 C1 *  8/1995

* cited by examiner

*Primary Examiner* — Keith Hendricks
*Assistant Examiner* — Steven A. Friday
(74) *Attorney, Agent, or Firm* — Bacon & Thomas, PLLC

(57) ABSTRACT

The invention relates to the method for producing high purity crystalline carbamide. The method comprises the crystallization and drying of carbamide, wherein an aqueous carbamide solution is preheated from +30° C. to +130° C., and thereafter the solution is purified by electrodialysis at a voltage in the range of 400 V-600 V. The technical result is the production of high-purity crystalline carbamide that can be used as an additive in the food industry and as a reagent in laboratory analyzes.

2 Claims, 2 Drawing Sheets

METHOD FOR PRODUCING HIGH PURITY CRYSTALLINE CARBAMIDE

The invention relates to the field of carbamide production, particularly to the method for producing high purity crystalline carbamide.

At the present time there are widely known methods for preparing granulated and crystalline carbamide. Industrial methods for producing carbamide arc based on the crystallization of aqueous carbamide solution obtained from carbon dioxide and ammonia. However, carbamide obtained by known methods does not have sufficient degree of purity for use in the food industry and for use as a reagent for laboratory analyses.

The closest technical solution chosen as a prototype is a method for producing crystalline carbamide obtained on the basis of carbon dioxide and ammonia (Patent RU 2041202). The method comprises crystallization of carbamide in the whole volume of the supersaturated solution, water removal from crystals to obtain compact mass, followed by removal of carbamide crystals by filtration and their drying. However, the obtained carbamide also does not have sufficient degree of purity for use in the food industry and for use as a reagent for laboratory analyses.

The object of the claimed invention is to provide a high purity crystalline carbamide.

The object is achieved by a method for producing high purity crystalline carbamide from an aqueous carbamide solution, comprising carbamide crystallization and drying according to the invention, the aqueous carbamide solution is heated to the temperature from +30° C. to +130° C., and thereafter the solution is purified by electrodialysis at a voltage in the range of 400 V-600 V, wherein the solution is heated to +30° C. at a concentration of 30%, to +40-50° C. at a concentration of 50%, to +70-80° C. at a concentration of 70%, to +90-130° C. at a concentration of 90% and higher.

Figure 1:
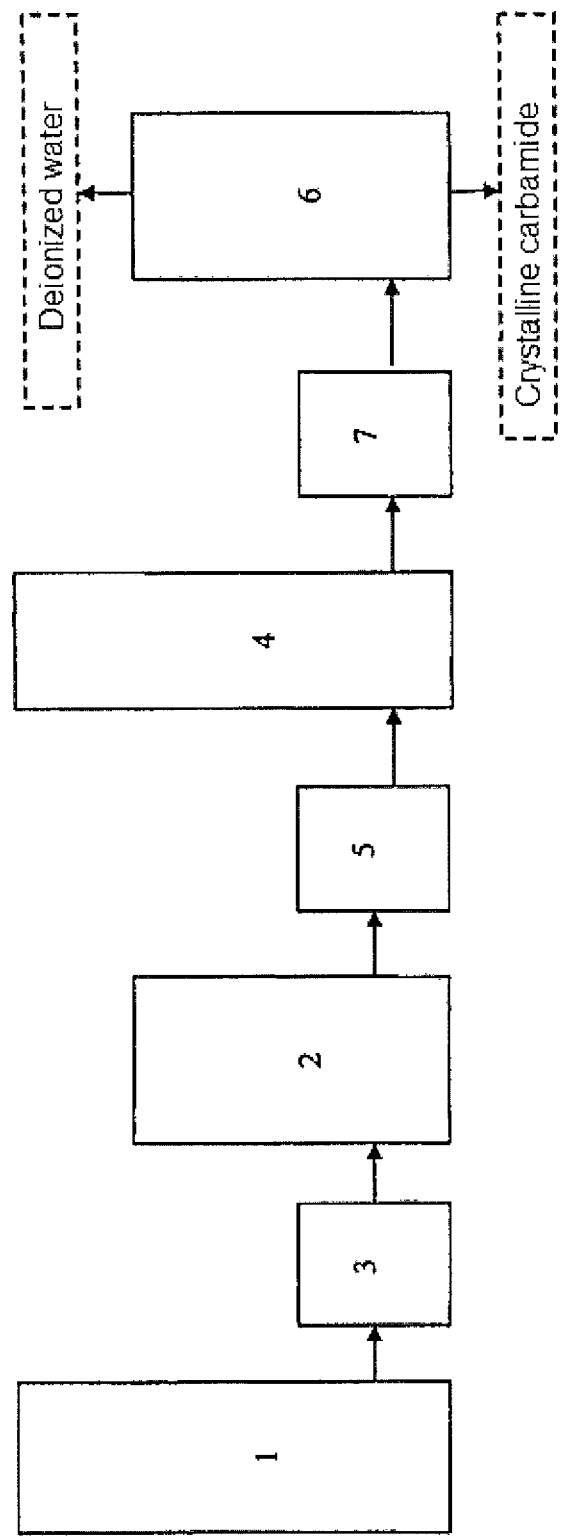
FIG. 1 shows a device for implementing the inventive method.

Device for implementing the inventive method is shown in FIG. 1. The device comprises a storage container 1 for the initial carbamide solution, electrodialysis unit 2, a pump 3 for supplying the solution from the container 1 to electrodialysis unit 2, a container 4 for the purified carbamide solution, a pump 5 for supplying the purified carbamide solution to the container 4, evaporation and crystallization unit 6, a pump 7 for supplying the purified carbamide from the container 4 to the evaporation and crystallization unit 6.

The method is performed as follows. The crude aqueous carbamide solution located in the storage container 1 is heated to the operating temperature from +30° C. to +130° C. to avoid early crystallisation of carbamide, wherein the solution is heated to +30° C. at a concentration of 30%, to +40-50° C. at a concentration of 50%, to +70-80° C. at a concentration of 70%, to +100-120° C. at a concentration of 90% and above. The relation between the concentration of the solution and the heating temperature thereof is determined empirically and is shown in FIG. 1.

Figure 2:
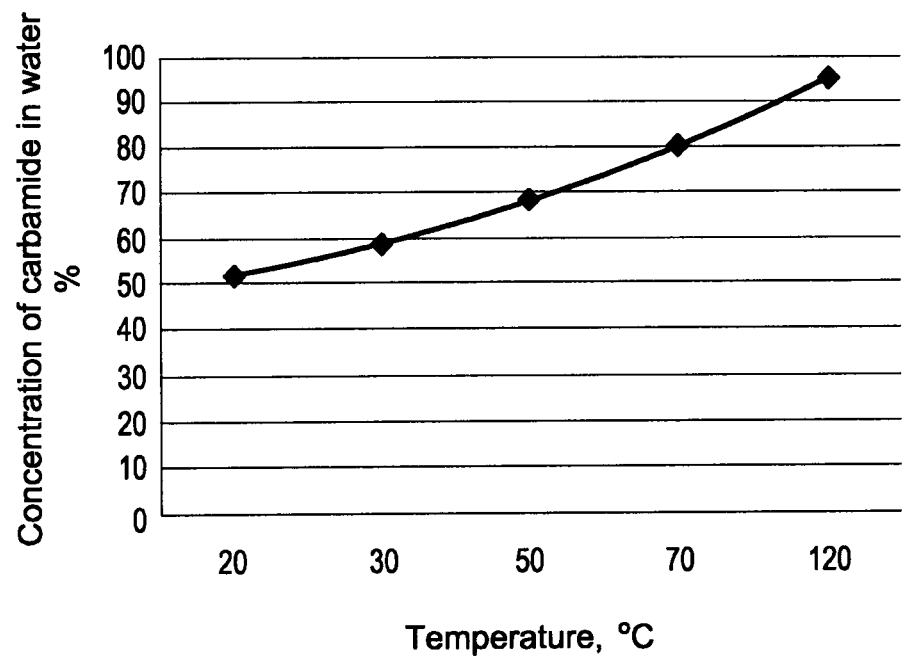
FIG. 2 shows a table that is a carbamide partially converted to crystalline state at the temperature of the carbamide solution less than 30° C.

As seen from the graph in FIG. 2, carbamide is partially converted to crystalline state at the temperature of the carbamide solution less than 30° C. Upon heating the solution above 130° C., a partial hydrolysis of urea occurs and it is dimerized to biuret, which content in the purified carbamide is strictly normalized.

Then the solution is supplied by the pump 3 to the electrodialysis unit 2. In the electrodialysis unit 2, salt-forming ions are removed from the solution by the electric current of 400V-600V. This range provides the optimal performance of the process: the amount/quality ratio. When the voltage is above 600V, the resulting product does not meet the requirements of the purified carbamide, applicable during laboratory analyses and in the food industry. When the voltage is below 400V, electrodialysis purification process is slow, so that the efficiency of the process is reduced. After deionization process, purified solution is supplied by the pump 5 to the storage container 4, and then is supplied by the pump 7 to the evaporation and crystallization unit 6, where the solution is separated to purified crystalline carbamide (carbamide crystallization) and deionized water. Carbamide crystallization with its simultaneous drying is performed by heating the solution to the temperature from 110° C. to 150° C. under atmospheric pressure or under vacuum pressure of 50-10 mm Hg. 50-80° C.

Quality parameters of carbamide obtained by the claimed method is shown in the Table 1.

TABLE 1

| Parameter name | Value |
| --- | --- |
| 1. Mass fraction of carbamide (CH4ON2), %, not less | 99.8 |
| 2. Melting temperature, ° C. | 132.7 ± 1 |
| 3. Mass fraction of water-insoluble components, %, up to | 0.003 |
| 4. Mass fraction of residues after baking (in the form of sulphates), %, up to | 0.01 |
| 6. Mass fraction of sulphates (SO4), %, up to | 0.001 |
| 7. Mass fraction of chlorides (Cl), %, up to | 0.0005 |
| 8. Mass fraction of ferrum (Fe), %, up to | 0.0001 |
| 9. Mass fraction of heavy metals (Pb), %, up to | 0.0002 |
| 10. Mass fraction of free ammonia (NH3), %, up to | 0.005 |
| 11. Mass fraction of biuret, %, up to | 0.1 |

Thus, the degree of purity of the obtained crystalline carbamide allows its use as an additive in the food industry (food additive E927b) and as a reagent for laboratory analyses.

Further, the obtained high purity crystalline carbamide is packaged in polypropylene bags or other similar containers. The obtained de-ionized water is a by-product with a target application: the use as a component of anti-freeze and non-freezing solution for windshields washer.

The invention claimed is:

1. A method for producing high purity crystalline carbamide from an aqueous carbamide solution, comprising carbamide crystallization and drying, characterized in that the aqueous carbamide solution is heated to a temperature from +30° C. to +130° C., whereupon the solution is purified by electrodialysis at a voltage in the range of 400V-600V.

2. The method according to claim 1, characterized in that the aqueous carbamide solution is heated to 30° C. at a concentration of 30%, to 50-60° C. at a concentration of 50%, to 70-80° C. at a concentration of 70%, to 90-130° C. at a concentration of 90% and higher.

* * * * *